United States Patent [19]

Vargiu et al.

[11] 3,960,981
[45] June 1, 1976

[54] MIXTURES OF VINYL ESTER RESINS

[75] Inventors: Silvio Vargiu, Sesto S. Giovanni (Milan); Edoardo Carpaneti, Genoa Bolzaneto; Beppino Passalenti, Milan, all of Italy

[73] Assignee: Societa' Italiana Resine S.I.R. S.p.A., Milan, Italy

[22] Filed: Dec. 27, 1974

[21] Appl. No.: 536,737

[30] Foreign Application Priority Data
Dec. 28, 1973   Italy .................................. 32341/73

[52] U.S. Cl. .............................. 260/837 R; 260/836
[51] Int. Cl.² ........................................ C08L 63/10
[58] Field of Search ......... 260/47 EP, 836 R, 837 R

[56] References Cited
UNITED STATES PATENTS

| | | | |
|---|---|---|---|
| 3,256,226 | 6/1966 | Fekete et al. | 260/837 R X |
| 3,377,406 | 4/1968 | Newey et al. | 260/836 X |
| 3,683,045 | 8/1972 | Baldwin | 260/837 R |
| 3,792,006 | 2/1974 | Najvar | 260/837 R |
| 3,816,283 | 6/1974 | Mani | 260/837 R X |
| 3,825,522 | 7/1974 | Vargiu et al. | 260/47 EP |

*Primary Examiner*—Lewis T. Jacobs
*Assistant Examiner*—S. M. Person
*Attorney, Agent, or Firm*—Holman & Stern

[57] ABSTRACT

An insaturated polyester A of the formula:

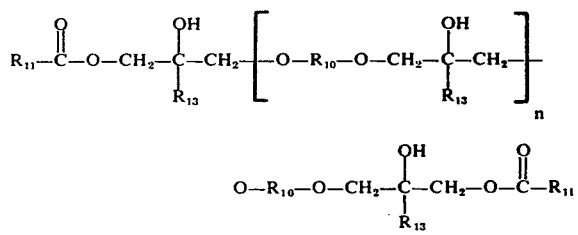

wherein n is an integer from 0 to 15,

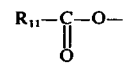

is the acid radical of an unsaturated monocarboxylic acid or of a monoester of an unsaturated bicarboxylic acid, $R_{13}$ is H or $CH_3$, and $R_{10}$ is an organic radical of a glycol HO-$R_{10}$-OH representated by the formulae:

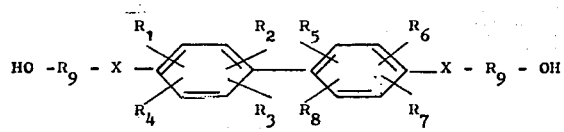

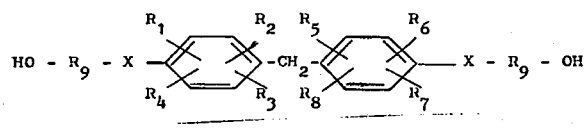

wherein:
$R_1$ is chlorine or bromine,
$R_2$, $R_3$, $R_4$, $R_5$, $R_6$, $R_7$, $R_8$ are hydrogen or bromine or chlorine,
X is a NH radical or oxygen,
$R_9$ is an alkyl or oxyalkyl radical containing 2 to 8 carbon atoms.

The solutions in an unsaturated solvent of said polyester A or of mixtures of polyester A with other unsaturated polyesters can harden, giving products of improved mechanical and self-extinguishing properties.

5 Claims, No Drawings

MIXTURES OF VINYL ESTER RESINS

The invention relates to novel unsaturated polyesters, obtained by reaction of a polyepoxide with an unsaturated monocarboxylic acid or with a monoester of an unsaturated dicarboxylic acid.

The invention further relates to the hardnable solutions of said unsaturated polyesters in an insaturated solvent.

The invention further relates to novel hardnable compositions comprising said unsaturated polyesters and other unsaturated polyesters in solution in an insaturated solvent.

As is well known, the products obtained by hardening of the polyepoxides exhibit various desirable properties such as proofness against solvents and chemical agents, respectively, and adhesion to metals.

It was therefore attempted at transferring the said desirable properties to conventional unsaturated polyester resins. To this end a polyepoxide is reacted with an unsaturated monocarboxylic acid, such as acrylic or methacrylic acid.

This reaction between the oxiranic bridge of the polyepoxide and the carboxylic group of the unsaturated monocarboxylic acid leads to the formation of an unsaturated polyester soluble in styrene, the said solution being hardenable by a peroxide catalyst, similarly to convention unsaturated polyester resins.

Hardening occurs by cross-linking by means of the double bond of the styrene and those of the unsaturated polyester.

A valuable unsaturated polyester known in the art is, for instance, that obtained by reaction of methacrylic acid with the diglycidyl ether of the 2,2-bis(4-hydroxy phenol) propane, which can be shown by the formula:

$$CH_2=C-C-O-CH_2-CH-CH_2-O-R-O-CH_2-CH-CH_2-O-C-C=CH_2 \quad (1)$$
$$\phantom{CH_2=}\,|\phantom{C-O-CH_2-}|\phantom{H-CH_2-O-R-O-CH_2-}|\phantom{H-CH_2-O-C-}|$$
$$\phantom{CH_2=}CH_3\phantom{C-O-CH_2-}OH\phantom{-CH_2-O-R-O-CH_2-}OH\phantom{-CH_2-O-C-}CH_3$$

wherein O-R-O denotes the 2,2-bis(4-hydroxyphenol)-propane group.

The styrene solution of the said unsaturated polyester hardens by the action of a peroxide to form a product exhibiting the desirable properties of the polyepoxides as well as those of conventional unsaturated polyester resins. However, the properties of such hardened products are not all fully satisfactory, more particularly the bending strength and the modulus of elasticity, which limits the use of such products in actual practice.

Moreover, the hardened products exhibit rather low values of the thermal distortion temperatures and do not possess the fire-proof or at least the self-extinguishing properties required for various end uses.

These drawbacks are obviated or at least substantially reduced by the use of the unsaturated polyester A of the invention, either in solution in an insaturated solvent or in mixture with another unsaturated polyester B in the said solvent.

An object of the invention is to provide the said novel unsaturated polyester A.

Another object of the invention is to provide a solution A of said polyester A in an insaturated solvent.

A further object of the invention is to provide a solution A-B comprising a mixture in said solvent of said polyester A with another unsaturated polyester B.

UNSATURATED POLYESTER A

It consists of the reaction product of an unsaturated monocarboxylic acid or of a monoester of an unsaturated dicarboxylic acid with the polyepoxide obtained starting from epichlorohydrin or methyl epichlorohydrin and a halogenated glycol selected among those which can be defined by the following general formulae:

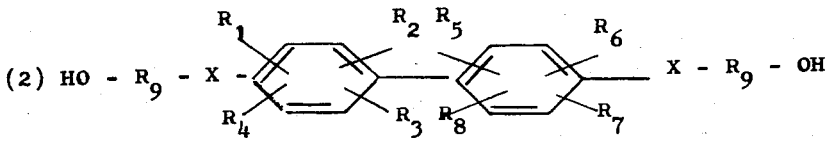

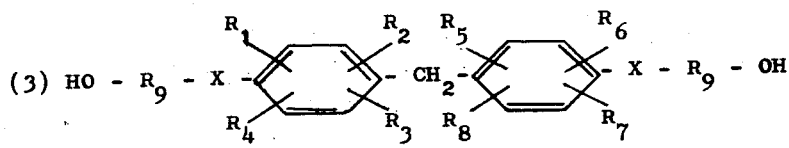

wherein $R_1$ stands for chlorine or bromine; $R_2$, $R_3$, $R_4$, $R_5$, $R_6$, $R_7$, $R_8$ stand for hydrogen or chlorine or bromine; X stands for a NH radical or oxygen; $R_9$ is an alkyl or oxyalkyl radical containing 2 to 8 carbon atoms.

For the sake of simplicity, the monomers indicated by formulae (2) and (3) shall be referred to hereafter as glycols.

Moreover, the reaction of the said glycol with epichlorohydrin or methyl epichlorohydrin yields a polyepoxide which can be represented by the following general formula:

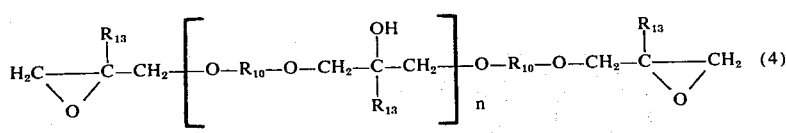

wherein O-$R_{10}$-O is the glycol, group n is an integer from 0 to 15, and $R_{13}$ is H or a $CH_3$ radical.

Finally, reaction of the polyepoxide represented by formula (4) with the unsaturated monocarboxylic acid or with the monoester of the unsaturated bicarboxylic acid yields the unsaturated polyester A of the invention which can be defined by the following general formula:

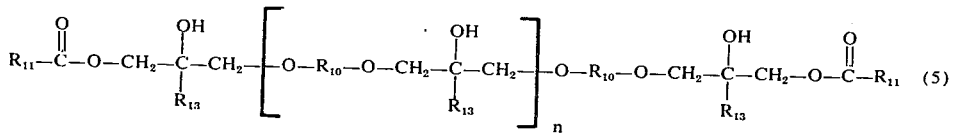

wherein $R_{10}$, n and $R_{13}$ have the same meaning as described in respect of formula (4),

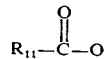

denoting the radical of the unsaturated carboxylic acid or of the monoester of the unsaturated bicarboxylic acid.

PREPARATION OF THE UNSATURATED POLYESTER A

The said preparation comprises a first step in which a polyepoxide is first prepared by reacting epichlorohydrin or methylepichlorohydrin with the above described glycols, followed by a dehydrochlorination treatment.

More particularly, the preferred glycols are: 4,4'-bis(diethylene glycol)-octachlorobiphenyl; N,N,',4,4'-bis-(2-hydroxyethylamino)-octachlorobiphenyl; glycols derived from decachlorobiphenyl such as by reaction with diols or aminoalcohols; glycols derived from octachloro-4,4'-dihydroxy-biphenyl, glycols derived from p,p', o,o' tetrabromodiphenylmethane and glycols derived from 4,4'-diamino-tetrabromodiphenylmethane.

The said glycols and epichlorohydrin or methylepichlorohydrin are first reacted in the presence of a coupling catalyst, especially boron trifluoride, preferably in the form of boron trifluoride etherate.

The temperature adopted is 130°–150°C, and epichlorohydrin or methylepichlorohydrin is slowly added to the reacting mass.

According to a preferred embodiment, the glycol is charged to the reaction vessel and boron trifluoride is added in a proportion of from 0.01 to 0.5 percent by weight with respect to the glycol. Epichlorohydrin or methylepichlorohydrin is then added during a period of 6 to 16 hrs, up to a total proportion of from 3.0 to 6.5 moles to one mole glycol, the thermal effect of the reaction being controlled during this period in order to maintain the temperature within the desired range.

On completion of the reaction, the mass is admixed with an inorganic base, such as sodium or potassium hydroxide in a solid finely subdivided form, preferably in a proportion of 2 to 3 moles to one mole glycol. The inorganic base is homogeneously dispersed and contact is maintained during 4 to 8 hours at a temperature preferably of the order of 130°–140°C. On completion of the treatment, the mass is extracted by means of an organic solvent such as toluene, xylene, or acetone, the solvent being evaporated from the extracted phase at subatmospheric pressure.

The resulting polyepoxide typically exhibits properties within the following ranges:
epoxy equivalent: 550–650
viscosity at 25°C at 70% in butyl "Carbitol" (R.T.M.): 150:250 cps.

The polyepoxide is then reacted with an unsaturated monocarboxylic acid or with a monoester of an unsaturated bicarboxylic acid, said acid being preferably selected among acrylic acid, methacrylic acid, crotonic acid, itaconic acid, methyl monomaleate and methyl monofumarate.

For said reaction, the reagents are supplied to a reactor and contacted at a temperature of from 120 to 150°C for a period of from 1 to 6 hours. The reaction is generally carried out in the presence of a catalyst of any of the following types: sodium carbonate, sodium acetate, ammonium carbonate, potassium carbonate, lithium carbonate, carbonates or acetates of alkaline earth metals, such as calcium and magnesium. Satisfactory results are obtained by employing a proportion of catalyst of from 1.8 to 6 moles to 100 moles unsaturated acid or monoester of the unsaturated bicarboxylic acid.

Moreover, the feeds to the reactor are controlled to afford a molar ratio of polyepoxide to unsaturated monocarboxylic acid or monoester of the unsaturated bicarboxylic acid of from ½ to 1/2.5. In actual practice, the reaction is pursued till the acid number of the reaction medium is equal to or lower than 10, said acid number being expressed in mg potassium hydroxide employed to neutralize one gram reaction product. The resulting unsaturated polyester A is dissolved in an insaturated solvent to form the solution A of the invention.

The solution A of the invention comprises the said polyester A in an insaturated solvent. More particularly, the said solvent is chosen among unsaturated monomers known in the art, capable of interacting with conventional unsaturated polyester resins. Examples of said solvents are styrene, vinyl toluene, alpha-methyl styrene, methyl methacrylate, diallyl phthalate, vinylcyclohexene. The preferred unsaturated solvent for the purposes of the invention is styrene. The preferred solution of polyester A comprises from 30 to 80 percent by weight of styrene, referred to the weight of the solution.

The solution of polyester A in styrene exhibit properties which are typically within the following ranges:

| | | |
|---|---|---|
| Dry residue | 20–70% | by weight |
| Viscosity at 25°C | 10–100 | cps |
| Gel at 25°C | 3–40 | minutes |
| Gel S.P.I. | 2–15 | minutes |

The solution A-B of the invention comprises a mixture in the said unsaturated solvent of the unsaturated polyester A of the invention with another polyester B.

More particularly, the said polyester A is present in the mixture in a weight ratio of the unsaturated polyester A to unsaturated polyester B ranging from 1:100 to 30:100.

Generally, the solvent used in said solution A-B is styrene, preferably in a proportion of from 30 to 50 percent by weight, referred to the weight of the solution.

The polyester B consists of the reaction product of an unsaturated monocarboxylic acid or of a monoester of an unsaturated bicarboxylic acid with the polyether glycidyl of the 2,2-bis(4-hydroxyphenol) propane. For the sake of simplicity the 2,2-bis(4-hydroxyphenol)-propane shall be referred hereafter as bisphenol A.

Moreover, the glycidyl polyether of bisphenol A can be shown by the following general formula:

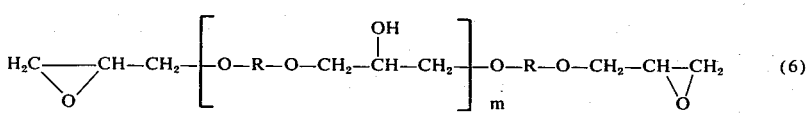

wherein O-R-O is the bisphenol A group and m is an integer from 0 to 20.

Finally, reaction of the polyepoxide shown in formula (6) with an unsaturated monocarboxylic acid or with a monoester of the unsaturated bicarboxylic acid yields the unsaturated polyester B which can be defined by the following general formula:

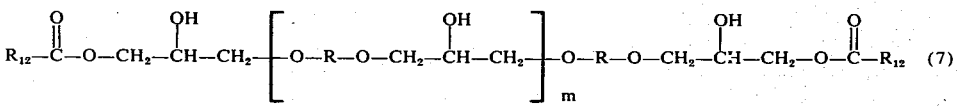

wherein R and m have the same meaning as described in respect of formula (6) and

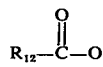

denotes the radical of an unsaturated monocarboxylic acid or of a monoester of the unsaturated bicarboxylic acid.

PREPARATION OF THE UNSATURATED POLYESTER B

The preparation of the unsaturated polyester B is carried out by first forming the polyglycidyl ether of bisphenol A.

To this end, a process known in the art can be adopted, in which epichlorohydrin and bisphenol A are charged to a reactor and contacted in a molar ratio of the order of 8:1 – 10:1, in the presence of an inorganic base used in a proportion of 2.0 to 2.5 moles to one mole bisphenol A.

Thus, e.g., an aqueous concentrated solution of the inorganic base can be added to the solution of bisphenol A in epichlorohydrin at a rate and a temperature such that the water introduced together with the base is azeotropically distilled with epichlorohydrin.

Alternatively, the reaction of bisphenol A and epichlorohydrin can be carried out within a range of temperature in which the reagents substantially do not boil, though the temperature is generally not sunk below 80°C.

At any rate, on completion of the reaction, the unreacted epichlorohydrin is separated generally by distillation and the alkali chloride obtained as side product of the reaction is separated from the distillation residue.

This stage can be operated with the polyglycidyl ether of bisphenol A dissolved in a solvent such as toluene. The latter is ultimately removed and a polyglycidyl ether of bisphenol A is obtained, having typically properties within the following ranges:
epoxy equivalent: 180 – 270
viscosity: 3,000 – 50,000 cps.

This polyglycidyl ether of bisphenol A of low epoxy equivalent is useful for the reaction with an unsaturated acid or with the monoester of an unsaturated dicarboxylic acid.

According to a further embodiment, the value of the epoxy equivalent is raised by reacting the previously described polyglycidyl ether with a further quantity of bisphenol A.

For this purpose, the processes known in the art can be employed, by which polyglycidyl ethers of bisphenol-A can be obtained with values of the epoxy equivalent exceeding 270 up to 4,500, semi-solid to solid in appearance.

These polyglycidyl ethers of bisphenol-A of high epoxy equivalent are likewise useful for reaction with an unsaturated acid or with the monoester of an unsaturated bicarboxylic acid, the conditions adopted being similar to those previously described in connection with the formation of the unsaturated polyester A.

The resulting unsaturated polyester B is mixed with the unsaturated polyester A and the whole is dissolved in the aforesaid solvent to give the solution AB of the invention. According to a further embodiment, a solution of the polyester A in said solvent is prepared, and a solution of the polyester B in the same solvent is separately prepared.

The two solutions are then mixed to give the solution AB of the invention.

The styrene solutions of the unsaturated polyester B typically exhibit the following properties when the said polyester is obtained starting from the polyglycidyl ether of bisphenol-A of a low epoxy equivalent (from 180 to 270):

| Dry residue | 50–70% | by weight |
| Viscosity at 25°C | 100–350 | cps |
| Gel at 25°C | 3–40 | minutes |
| Gel S.P.I. | 2–20 | minutes |

When the polyglycidyl ether of bisphenol A is of a high epoxy equivalent (exceeding 270 up to 4,500) the styrene solutions of the corresponding unsaturated polyester B exhibit properties which typically fall within the following ranges:

| Dry residue | 50–70% | by weight |
| Viscosity at 25°C | 400–1000 | cps |
| Gel at 25°C | 2–30 | minutes |
| Gel S.P.I. | 2–25 | minutes. |

It should be noted that the solution of polyester A in an insaturated solvent can be used also for forming hardnable compositions including unsaturated polyesters similar in function to the said polyester B.

Thus, for example, such a polyester similar in function can be obtained by replacing epichlorohydrin by methylepichlorohydrin in the preparation of polyester B. Moreover, can be obtained by using further diphenols instead of bisphenol A, such as:

Bisphenol F (bis-(4-hydroxyphenyl)methane), resorcinol, pyrocatechol and hydroquinone, or compounds with more than two phenolic hydroxyls in the molecule. Moreover, it can also be obtained by using in the preparation of polyester B further diepoxides in lieu of the previously described glycidylpolyethers, such as epoxydated novolaks, epoxycycloaliphatic compounds, diepoxides obtained in the art by interaction of (non-halogenated) diols with epichlorohydrin or methylepichlorohydrin or, generally, all products containing two epoxy groups in the molecule.

The solution of polyester A of the invention hardens under the action of the peroxides and yields noninflammable products or products having self-extinguishing properties as a function of the halogen quantity contained therein.

Moreover, these hardened products exhibit high generic properties, more particularly in respect of bending strength modulus of elasticity and heat-distorsion temperature (H.D.T.). The composition of the invention is preferred and the corresponding hardened products are self-extinguishing and exhibit suprisingly high properties in respect of bending strength, modulus of elasticity and H.D.T.

The solutions of the invention can be hardened by the action of peroxides such as methyl ethyl ketone peroxide, cyclohexanone peroxide, benzoyl peroxide, cumene hydroperoxide and, generally, all substances of a peroxide nature employed in the art for hardening conventional unsaturated polyester resins.

More particularly, in hardening, a peroxide proportion of from 0.2 to 4.0 parts by weights to 100 parts by weight of the solution or composition is generally used.

The solution or composition can include hardening accelerators, such as dimethylaniline, trimethylbenzylammonium chloride in a proportion of from 0.1 to 2 parts by weight to 100 parts by weight of the composition.

It is also possible to use as accelerators salts of metals (such as cobalt and vanadium), such as naphthenates and octoates of cobalt, vanadium or vanadyl, or any accelerators which are normally employed in the art for conventional unsaturated polyester resins. These metal accelerators are usually employed in a proportion of from 0.02 to 2 parts by weight (in a solution comprising about 6 percent by weight of metal) to 100 parts by weight of the composition.

The solutions of the invention can be employed in the field of mastics, when they contain mineral fillers or for manufacturing reinforced plastics by impregnation of glass fibers with the said solutions.

They may be further employed for casting, and in this case the mineral filler can be optionally present. The major fields of use are manufacture of artefacts such as pipes, tanks or apparatus generally reinforced with glass exhibiting a high resistance against corrosion, formulation of low-shrinking mastics, and in the electrotechnical field where they afford a high resistance.

The following experimental examples will further illustrate the invention without, however, implying any limitation thereof.

EXAMPLE 1 (PREPARATION OF THE UNSATURATED POLYESTER B)

A flask equipped with a stirrer, a thermometer, a distiller and an inlet for the inert gas is charged with 684 parts by weight bisphenol A and 2,275 parts by weight epichlorohydrin.

The mass is stirred and heated to a temperature of 90°–95°C, maintaining an inert atmosphere. On reaching this temperature, 496 parts by weight aqueous sodium hydroxide (concentration 50 percent by weight approximately) are gradually added during 6 hours.

During the addition of aqueous sodium hydroxide, the water is azeotropically distilled with the epichlorohydrin.

On completion of the addition of aqueous sodium hydroxide, the mass is maintained at reflux during about 30 minutes. The unaltered epichlorohydrin is then distilled at subatmospheric pressure, and after cooling, the distillation residue is admixed with 1,200 parts by weight toluene, this leading to the separation of sodium chloride, and ultimately toluene is distilled off. The resulting liquid polyglycidyl ether of bisphenol A has the following properties:

| | |
|---|---|
| Viscosity in cps at 25°C | 15,500 |
| Molecular weight | 370–390 |
| Epoxy equivalent | 185–195 |

520 parts by weight glycidyl polyether of bisphenol A obtained as above are reacted in a closed vessel while stirring with 195 parts acrylicacid in the presence of 0.1 part by weight sodium carbonate till a maximum temperature of 150°C is obtained.

After 6 hours, the mass is cooled and a polyester B of the following properties is discharged. Acid number : below 0.1 equivalents / Gram Viscosity : 250–300 cps, measured at 25°C in a styrene solution of 70 percent by weight styrene.

EXAMPLE 2 (PREPARATION OF THE UNSATURATED POLYESTER A)

A flask equipped with a stirrer, a reflux cooler and a thermometer is charged with 638 parts by weight bis-(di-ethyleneglycol)-octachlorodiphenyl and heated in a nitrogen stream up to 140°C. During about 10 minutes, 2.0 grams boron trifluoride in the form of boron trifluoride etherate are added and homogenized.

400 parts by weight epichlorohydrin are added for about 10 hours and the heat evolved by the reaction is controlled, the temperature being maintained at the stated value, whereupon the mass maintained at 130°–140°C is admixed with 92 parts by weight sodium hydroxide in a solid powder form and maintained at this temperature during about 5 hours. The reaction mass is then extracted with xylene and the xylene is evaporated at subatmospheric pressure. This yields a liquid polyepoxide of the following properties:

| | |
|---|---|
| Viscosity at 25°C at 70% in butyl "Carbitol" (R.T.M.): | : 150–200 |
| Molecular wight | : 1,100–1,200 |
| Epoxy equivalent | : 550–600 |

560 parts by weight of the resulting polyepoxide are reacted with 100 parts by weight acrylic acid in the presence of 0.1 part by weight sodium carbonate up to a maximum temperature of 150°C. After six hours, the polyester A is cooled and discharged and exhibits the following properties: Acid number : below 0.1 equivalents/ gram Viscosity: 40–50 cps measured at 25°C in a styrene solution at 70 percent by weight styrene.

EXAMPLE 3

The unsaturated polyester A prepared in accordance with Example 2 is dissolved in styrene to a concentration of the latter amounting to 30 percent in the solution. The same is effected with the unsaturated polyester B prepared according to Example 1.

Compositions are then prepared having different proportions of the two described solutions.

Table 1 summarizes the compositions and properties of the solutions.

All tested solutions (a to e) shown in Table 1 are submitted to hardening starting from 100 parts by weight, solution of unsaturated polyester in styrene, 1.5 parts by weight methyl ethyl ketone peroxide (50 percent by weight) and 0.2 part by weight cobalt octoate (6 percent by weight metal). The solution used in Test b is a comparative one.

Hardening is carried out at room temperature during 24 hours and at 125°C during 15 minutes.

Table 1

| Composition | Test a | Test b | Test c | Test d | Test e |
| --- | --- | --- | --- | --- | --- |
| Solution of unsaturated Polyester A containing 30% styrene (parts by weight) | 100 | 0 | 5 | 10 | 20 |
| Solution of unsaturated polyester B containing 30% styrene (parts by weight) | 0 | 100 | 95 | 90 | 80 |
| PROPERTIES | | | | | |
| % by weight solids | 70 | 70 | 70 | 70 | 70 |
| Viscosity in cps at 25°C | 45 | 260 | 180 | 145 | 100 |
| Gardner colour number | 6 | 3 | 3 | 4 | 4 |
| Gel at 25°C | 9' | 6'15" | 6'50" | 8'10" | 9' |
| Gel S.P.I. | 7' | 8'50" | 9' | 8'15" | 9'35" |

The sample from (Test a) did not burn. The flammability (Method ASTM D-635) expressed in mm/minute determined on the remaining samples was 35.8 (Test b), 25.7 (Test c), 10.3 (Test d) and 4.1 (Test e).

EXAMPLE 4

An unsaturated polyester B is prepared from acrylic acid and polyglycidyl ether of 2,2-bis-(4-hydroxyphenyl)-propane.

The latter is prepared from bisphenol A and epichloro hydrin and exhibits the following properties: molecular weight 950–1,050, epoxy equivalent 480–520. 530 parts by weight of the said polyglycidyl ether of bisphenol A are reacted with 75 parts by weight acrylic acid in the presence of 0.05 part by weight sodium carbonate up to a maximum temperature of 150°C.

Cooling is effected after four hours and the resulting unsaturated polyester B has an acid number below 0.1 equivalent/gram and a viscosity of 620–650 cps (measured in a styrene solution at 60 percent by weight styrene).

EXAMPLE 5

The unsaturated polyester B prepared as described in Example 4 is dissolved in styrene to a concentration of the latter amounting to about 40 percent in the solution.

Similarly, the unsaturated polyester A of Example 2 is dissolved in styrene to a concentration of the latter amounting to 30 percent in the solution.

Compositions having different proportions of the two described solutions are prepared, adding if desired further quantities of styrene in order to bring its content to the desired value.

Table 2 summarizes the composition and properties of the said solutions, Test a being effected on a comparative solution not including A.

Table 2

| COMPOSITION (parts by weight) | Test a | Test b | Test c | Test d |
| --- | --- | --- | --- | --- |
| Solution of unsaturated polyester B containing 40% styrene | 100 | 95 | 90 | 80 |
| Solution of unsaturated polyester A containing 30% styrene | 0 | 4.28 | 8.57 | 17.15 |
| Added styrene | 0 | 0.72 | 1.43 | 2.85 |
| PROPERTIES | | | | |
| % by weight solids | 60 | 60 | 60 | 60 |
| Viscosity at 25°C in cps | 640 | 510 | 320 | 200 |
| Gardner colour number | 3 | 3 | 4 | 4 |
| Gel at 25°C | 6'15" | 4'35" | 14' | 14' |
| Gel S.P.I. | 7' | 7' | 7'30" | 7'10" |

All compositions (a to d) previously described are submitted to hardening, starting from 100 parts by weight composition, 1.5 parts by weight methyl ethyl ketone peroxide (50 percent by weight) and 0.2 parts by weight cobalt octoate at 6 percent by weight metal.

Hardening is carried out at room temperature for 24 hours, at 65°C for 2 hours, at 80°C for 2 hours and at 150°C for 4 hours.

The samples are tested for bending strength properties (ASTM D 256), modulus of elasticity (ASTM D 790) and H.D.T. (ASTM D 648).

The results are summarized in Table 3, wherein Test a is comparative Test.

Table 3

| | Test a | Test b | Test c | Test d |
| --- | --- | --- | --- | --- |
| Bending strength kg/sq.cm | 694 | 750 | 825 | 740 |
| Modulus of elasticity kg/sq.cm $10^3$ | 31.7 | 33.4 | 35.7 | 34.9 |
| H.D.T. (°C) | 56 | 75 | 82 | 80 |

We claim:
1. An unsaturated organic solvent solution of a mixture of polyesters comprising a first polyester of the formula:

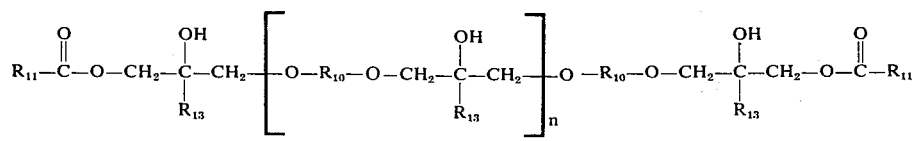

wherein:
n is an integer from 0 to 15,
$R_{13}$ is a radical selected from the group consisting of H and $CH_3$,

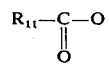

is a member of the group consisting of ethylenically unsaturated monocarboxylic acids and monoesters ethylenically unsaturated dicarboxylic acids,
$R_{10}$ is the organic radical of a glycol HO-$R_{10}$-OH selected from the group consisting of:

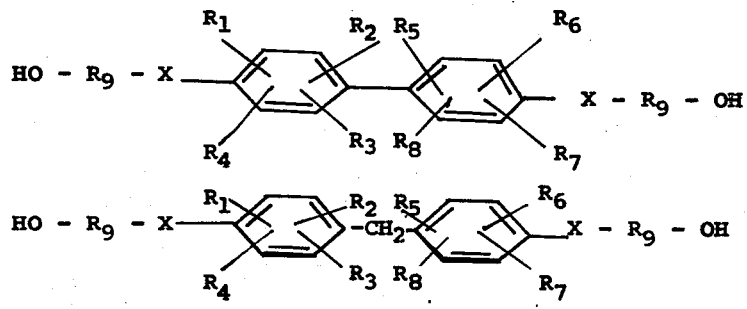

wherein:
$R_1$ is chlorine or bromine;
$R_2$, $R_3$, $R_4$, $R_5$, $R_6$, $R_7$, $R_8$ are radicals selected from the group consisting of hydrogen, bromine and chlorine radicals,
X is selected from the group consisting of the NH radical and oxygen,
$R_9$ is a radical selected from the group consisting of alkyl and oxyalkyl radicals containing 2 to 8 carbon atoms;
and a second polyester of the formula:

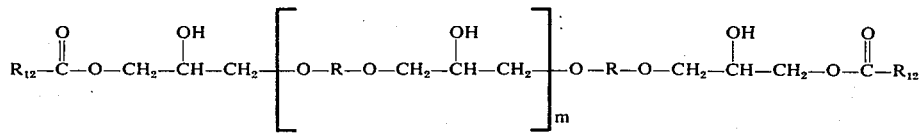

wherein:
m is an integer from 0 to 20
R is the bisphenyl radical corresponding to the bisphenol A

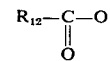

is a member of the group consisting of ethylenically unsaturated monocarboxylic acids and monoesters of ethylenically unsaturated dicarboxylic acids
said first polyester being present in the solution in a weight ratio of said first polyester to said second polyester of from 1:100 to .30:100.

2. The solution of claim 1, wherein the said acid radical of the polyester B is selected in the group consisting of those of acrylic acid, methacrylic acid, itaconic acid, crotonic acid, methyl monomaleate and methyl monofumarate.

3. The solution of claim 1, wherein the said solvent is selected in the group consisting of styrene, vinyl toluene, alpha-methyl styrene, methyl methacrylate, diallyl phthalate and vinylcyclohexane.

4. The solution of claim 1, wherein the said solvent is styrene.

5. The solution of claim 4, wherein the styrene is present in a proportion of from 30 to 50 percent by weight with respect to the weight of the solution.